US011478375B1

(12) United States Patent
Bailey

(10) Patent No.: US 11,478,375 B1
(45) Date of Patent: Oct. 25, 2022

(54) DIGIT WRAPPING ASSEMBLY AND METHOD

(71) Applicant: Mary C. Bailey, Jacksonville Beach, FL (US)

(72) Inventor: Mary C. Bailey, Jacksonville Beach, FL (US)

(*) Notice: Subject to any disclaimer, the term of this patent is extended or adjusted under 35 U.S.C. 154(b) by 1171 days.

(21) Appl. No.: 15/367,132

(22) Filed: Dec. 1, 2016

Related U.S. Application Data

(60) Provisional application No. 62/342,553, filed on May 27, 2016.

(51) Int. Cl.
*A61F 5/058* (2006.01)
*A61F 5/01* (2006.01)

(52) U.S. Cl.
CPC ........ *A61F 5/05875* (2013.01); *A61F 5/0111* (2013.01); *A61F 5/0118* (2013.01)

(58) Field of Classification Search
CPC .. A61F 5/05875; A61F 5/0111; A61F 5/0118; A61F 5/00; A61F 5/0104; A61F 5/01; A61F 5/04; A61F 5/05; A61F 5/058; A61F 5/05825; A61F 5/05841; A61F 5/05866; A61F 5/10; A61F 5/0109; A61F 13/00; A61F 13/00004; A61F 13/00008; A61F 13/00021; A61F 13/00025; A61F 13/00029; A61F 13/00038; A61F 13/10; A61F 13/104; A61F 13/105; A61F 13/063; A61F 13/068
USPC .... 602/22, 30, 11, 3, 23, 24, 25, 28, 29, 31; 128/893
See application file for complete search history.

(56) References Cited

U.S. PATENT DOCUMENTS

| | | | |
|---|---|---|---|
| 2,354,770 A * | 8/1944 | Maisie | A61F 5/019 602/30 |
| 2,471,997 A | 5/1949 | Baltor | |
| 5,695,453 A | 12/1997 | Neal | |
| 5,993,405 A | 11/1999 | Wynn | |
| 7,011,641 B1 | 3/2006 | De Toro et al. | |
| 7,169,121 B2 | 1/2007 | Berrehail | |
| 7,780,615 B1 * | 8/2010 | Shesol | A61F 13/105 602/22 |
| 8,795,247 B2 | 8/2014 | Bennett et al. | |
| 2004/0019308 A1 | 1/2004 | Chow | |
| 2007/0135747 A1 | 6/2007 | Chan | |
| 2011/0306912 A1 | 12/2011 | Heckel | |

* cited by examiner

*Primary Examiner* — Erin Deery
*Assistant Examiner* — Robin Han
(74) *Attorney, Agent, or Firm* — John Rizvi; John Rizvi, P.A. The Patent Professor

(57) ABSTRACT

Disclosed is a digit wrapping assembly configured to wrap and compress digits in a foot or hand. A method of using the digit wrapping assembly may include, in a positioning state of the digit wrapping assembly, the first digit being vertically offset from the second and third digits, and in a securing state of the digit wrapping assembly, the first, second, and third digits being substantially vertically aligned with one another. The digit wrapping assembly may be configured to compress at least two, three, or four digits.

9 Claims, 6 Drawing Sheets

DIGIT WRAPPING ASSEMBLY AND METHOD

CROSS-REFERENCE TO RELATED APPLICATION

This application claims the benefit of U.S. Provisional Patent Application Ser. No. 62/342,553, filed May 27, 2016, which is incorporated herein in its entirety.

FIELD OF THE INVENTION

The present invention relates generally to immobilizing wraps for fingers and toes, and more particularly, to a digit wrapping assembly which is patient-adjustable and can be contoured to compress the fingers or toes of a patient in therapeutic, pre-surgical and/or post-surgical applications. The invention also refers to a method for wrapping a person's fingers or toes using the digit wrapping assembly.

BACKGROUND OF THE INVENTION

Pressure wrap therapy has been utilized for the treatment of a variety of ailments by restricting movement and facilitating alignment of bones and connective tissues. Typically, pressure wrap therapy is carried out by applying a flexible medical wrap around the area of the patient's body to be treated. Generally, medical wraps are placed by medical personnel and removed once they have stretched out or become soiled.

Pressure wrap therapy may be used in both pre-surgical and post-surgical applications. In the case of pre-surgical applications, pressure wraps and bindings may prevent movement as an alternative to surgical procedures or to alleviate symptoms until surgery. In the case of post-surgical applications, pressure wraps and bindings may be used to ensure that the wrapped portions of the body remain immobile while healing occurs. In both cases, swelling may cause the wrapped areas to increase in size, causing the pressure wrap to lose its effectiveness. Thus, the area must normally be rewrapped in order to maintain the benefits of the pressure wrap. Because continual or repeated rewrapping is typically performed in the office of a medical professional, the overall cost of pressure wrap therapy is considerably high and may render the therapy impractical.

Conventional pressure wraps used in pressure wrap therapy are typically adapted for application to large areas and utilize stretchable materials to achieve a contoured fit. In addition, conventional pressure wraps generally require tape, clips or hook-and-loop closures to secure the wraps. For application to smaller areas such as fingers and toes, conventional wraps are found to be bulky and cumbersome to apply, and cannot be contoured to effectively restrict movement of injured or impaired areas.

Accordingly, there is an established need for a wrap which is particularly designed for applying pressure wrap therapy to a patient's fingers or toes, and which can be contoured to adequately compress the fingers or toes of a patient in therapeutic, pre-surgical and/or post-surgical applications and can be easily adjusted by the patient if needed.

SUMMARY OF THE INVENTION

The present invention is directed to a digit wrapping assembly and method which is patient-adjustable and can be contoured to compress the fingers or toes of a patient in therapeutic, pre-surgical and/or post-surgical applications. The digit wrapping assembly is flexible and preferably non-stretchable, and includes a set of strap portions forming four individual loops for securing four digits in variable positions relative to one another. Opposite end straps can disconnectably attach to one another to secure and provide an adjustable overall compression to all four digits. The digit wrapping assembly and method are easily and intuitively usable by any person. The person wearing the digit wrapping assembly can adjust the degree of compression without requiring another person's assistance.

Introducing an illustrative embodiment of the invention, the present invention includes a digit wrapping assembly contoured to fit the fingers or toes of a user. The digit wrapping assembly comprises a flexible support. A flexible, first end strap portion extends from the support at or near a first longitudinal end thereof, and a flexible, second end strap portion extends from the support at or near an opposite, second longitudinal end thereof. A flexible, first intermediate strap portion and a flexible, second intermediate strap portion extend from an intermediate region of a top side of the support. In addition a flexible, first bottom strap portion and a flexible, second bottom strap portion extend from a bottom side of the support. The first intermediate strap portion and the first end strap portion face one another and are disconnectably attachable to one another to encircle a first space. The first bottom strap portion and the support face one another and are disconnectably attachable to one another to encircle a second space. The second bottom strap portion and the support face one another and are disconnectably attachable to one another to encircle a third space. The second intermediate strap portion and the second end strap portion face one another and are disconnectably attachable to one another to encircle a fourth space. The first end strap portion is extendable over and disconnectably attachable to the second end strap portion, to apply a compression on all four encircled spaces.

In another aspect, the digit wrapping assembly can include a plurality of hook-and-loop fasteners for disconnectably attaching the first intermediate strap portion to the first end strap portion, the first bottom strap portion to the support, the second bottom strap portion to the support, the second intermediate strap portion to the second end strap portion, and the first end strap portion to the second end strap portion.

In another aspect, the plurality of hook-and-loop fasteners can be selectively adjusted for tightness by a patient.

Introducing another embodiment of the invention, the present invention includes a method for wrapping and compressing a first digit, a second digit, a third digit and a fourth digit of a subject, comprising, providing a digit wrapping assembly including, a flexible support, a flexible, first end strap portion extending from the support at or near a first longitudinal end thereof, and a flexible, second end strap portion extending from the support at or near an opposite, second longitudinal end thereof, a flexible, first intermediate strap portion and a flexible, second intermediate strap portion extending from an intermediate region of a top side of the support, a flexible, first bottom strap portion and a flexible, second bottom strap portion extending from a bottom side of the supports, extending the first and second bottom strap portions between the second and third digits, extending the first and second bottom strap portions around the second and third digits, respectively, fastening the first bottom strap portion to the support, encircling the second digit, fastening the second bottom strap portion to the support, encircling the third digit, extending the second intermediate strap portion and the second end strap portion around the fourth digit, fastening the second intermediate strap portion to the second end strap portion, encircling the fourth digit, extending the first intermediate strap portion and the first end strap portion around the first digit, fastening the first intermediate strap portion to the first end strap portion, encircling the first digit, and attaching the first end strap portion to the second end strap portion.

Disclosed is a digit wrapping assembly, comprising, a support strap comprising a first support strap portion and a second support strap portion, a digit wrapping sub-assembly for a first digit disposed on a top surface of the support strap, the digit wrapping sub-assembly for the first digit comprising variably anglable opposing faces, a digit wrapping sub-assembly for a second digit comprising a variably anglable face opposing a bottom surface of the first support strap portion, and a digit wrapping sub-assembly for a third digit comprising a variably anglable face opposing a bottom surface of the second support strap portion, wherein each of the variably anglable faces comprises a fastener configured for disconnectable attachment with a corresponding fastener, in a positioning state of the digit wrapping assembly, the first digit is vertically offset from the second and third digits, and in a securing state of the digit wrapping assembly, the first, second, and third digits are substantially vertically aligned with one another.

In another aspect, the digit wrapping sub-assembly for the first digit comprises a first end strap portion opposing a first intermediate strap attachment portion, the first end strap portion and the first intermediate strap attachment portion being separated from each other by a first strap attachment portion.

In another aspect, the first strap attachment portion is disposed on a top surface of the first support strap portion toward a distal end of the support strap.

In another aspect, the first end strap portion and the first intermediate strap attachment portion comprise respective opposing fasteners configured for disconnectable attachment with each other.

In another aspect, the digit wrapping assembly further comprises a digit wrapping sub-assembly for a fourth digit disposed on the top surface of the support strap, the digit wrapping sub-assembly for the fourth digit comprising variably anglable opposing faces configured for disconnectable attachment with one another.

In another aspect, one of the variably anglable opposing faces of the digit wrapping sub-assembly for the fourth digit is configured for disconnectable attachment with one of the variably anglable opposing faces of the digit wrapping sub-assembly for the first digit.

In another aspect, the digit wrapping sub-assembly for the fourth digit comprises a second end strap portion opposing a second intermediate strap attachment portion, the second end strap portion and the second intermediate strap attachment portion being separated from each other by a second strap attachment portion.

In another aspect, the second strap attachment portion is disposed on a top surface of the second support strap portion toward a distal end of the support strap.

In another aspect, the fastener of the variably anglable face of the digit wrapping sub-assembly for the second digit is configured for disconnectable attachment with a fastener disposed on the bottom surface of the first support strap portion, and wherein the fastener of the variably anglable face of the digit wrapping sub-assembly for the third digit is configured for disconnectable attachment with a fastener disposed on the bottom surface of the second support strap portion.

Disclosed is a method of securing digits of a user in a digit wrapping assembly, comprising, positioning a first digit of the user in a first space delimited between a first end strap portion and a first intermediate strap portion of the digit wrapping assembly, positioning a second digit of the user in a second space delimited between a first support strap portion and a first bottom strap portion of the digit wrapping assembly, positioning a third digit of the user in a third space delimited between a second support strap portion and a second bottom strap portion of the digit wrapping assembly, positioning a fourth digit of the user in a fourth space delimited between a second end strap portion and a second intermediate strap portion and of the digit wrapping assembly, and at least partially enclosing one or more of the first, second, third, and fourth spaces to thereby secure and compress one or more of the first, second, third, and fourth digits therein, respectively.

In another aspect, positioning the second digit in the second space and positioning the third digit in the third space comprise inserting the first and second bottom strap portions between the second and third digits.

In another aspect, the second and third spaces are both arranged longitudinally between the first and fourth spaces.

In another aspect, positioning the first and fourth digits comprises positioning the first and fourth digits above a support strap, and wherein positioning the second and third digits comprises positioning the second and third digits below the support strap.

In another aspect, in a positioning state of the digit wrapping assembly, the first and fourth digits are vertically offset from the second and third digits, and in a securing state of the digit wrapping assembly, the first, second, third, and fourth digits are substantially vertically aligned with one another.

In another aspect, at least partially enclosing the first space comprises disconnectably attaching fasteners respectively disposed on opposing surfaces of the first end strap portion and the first intermediate strap portion, and wherein at least partially enclosing the fourth space comprises disconnectably attaching fasteners respectively disposed on opposing surfaces of the second end strap portion and the second intermediate strap portion.

In another aspect, at least partially enclosing the second space comprises disconnectably attaching fasteners respectively disposed on opposing surfaces of the first bottom strap portion and the first support strap portion, and wherein at least partially enclosing the third space comprises disconnectably attaching fasteners respectively disposed on opposing surfaces of the second bottom strap portion and the second support strap portion.

In another aspect, the method further comprises, after at least partially enclosing the first and fourth spaces, disconnectably attaching fasteners respectively disposed on opposing surfaces of the first end strap portion and the second end strap portion.

In another aspect, the method further comprises, adjusting a level of compression applied to the first, second, third, and fourth digits by the digit wrapping assembly by adjusting a degree of overlap between the fasteners when attached to each other.

Disclosed is a digit wrapping assembly contoured to fit the fingers or toes of a user, comprising, a flexible support, a flexible, first end strap portion extending from the support at or near a first longitudinal end thereof, and a flexible, second end strap portion extending from the support at or near an opposite, second longitudinal end thereof, a flexible, first intermediate strap portion and a flexible, second intermediate strap portion extending from an intermediate region of a top side of the support and a flexible, first bottom strap portion and a flexible, second bottom strap portion extending from a bottom side of the support, wherein the first intermediate strap portion and the first end strap portion face one another and are disconnectably attachable to one another to encircle a first space, the first bottom strap portion and the support face one another and are disconnectably attachable to one another to encircle a second space, the second bottom strap portion and the support face one another and are disconnectably attachable to one another to encircle a third space, the second intermediate strap portion and the second end strap portion face one another and are disconnectably attachable to one another to encircle a fourth space, and the first end strap portion is extendable over and attachable to the second end strap portion.

In another aspect, in a positioning state of the digit wrapping assembly, the first and fourth spaces are vertically offset from the second and third spaces, in a securing state of the digit wrapping assembly, the first, second, third, and fourth spaces are substantially vertically aligned with one another, and a degree of overlap between the first end strap portion and the second end strap portion is adjustable to adjust a degree of compression applied to one or more digits respectively positioned in the first, second, third, and fourth spaces.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a digit wrapping assembly which is patient-adjustable and can be contoured to compress the fingers or toes of a patient in therapeutic, pre-surgical and/or post-surgical applications.

Figure 1:
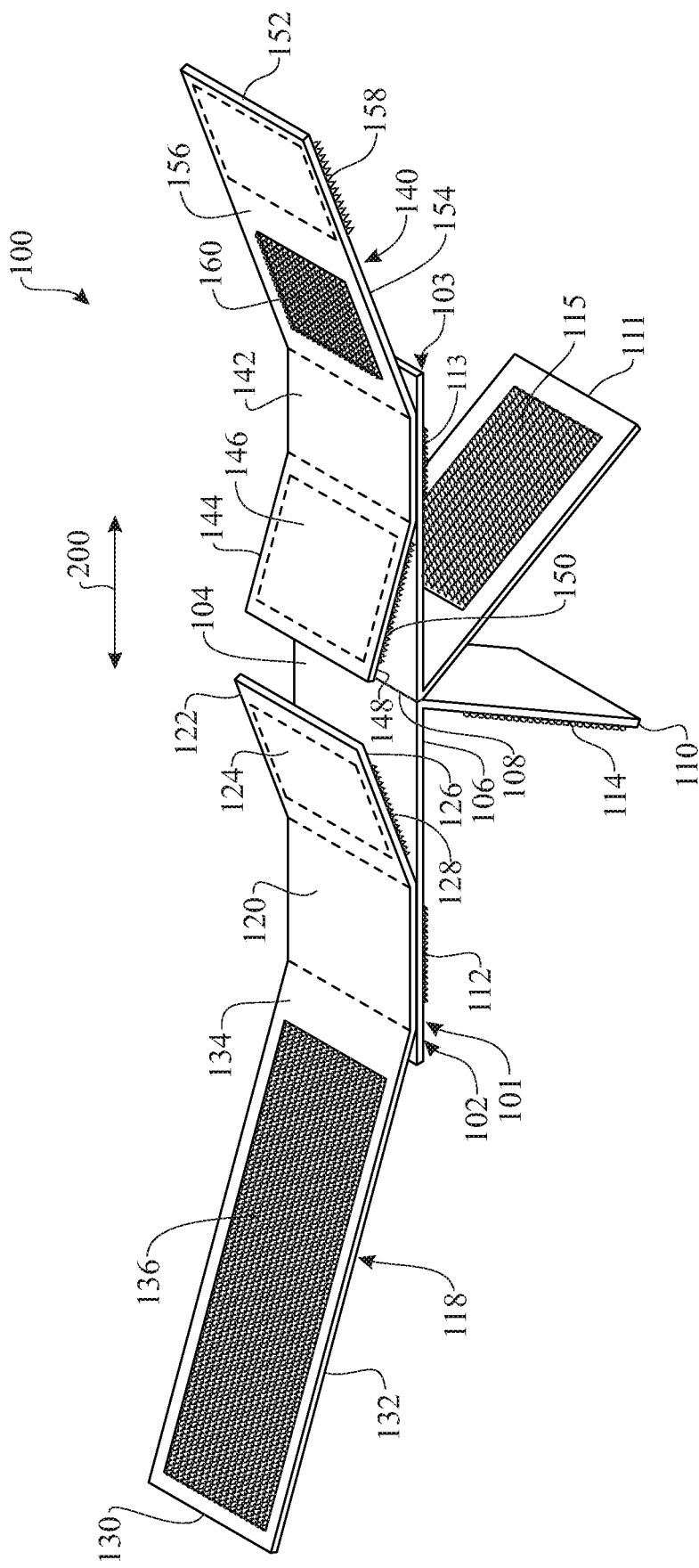
FIG. 1 presents a top front perspective view of a digit wrapping assembly in accordance with an illustrative embodiment of the present invention.
Figure 2:
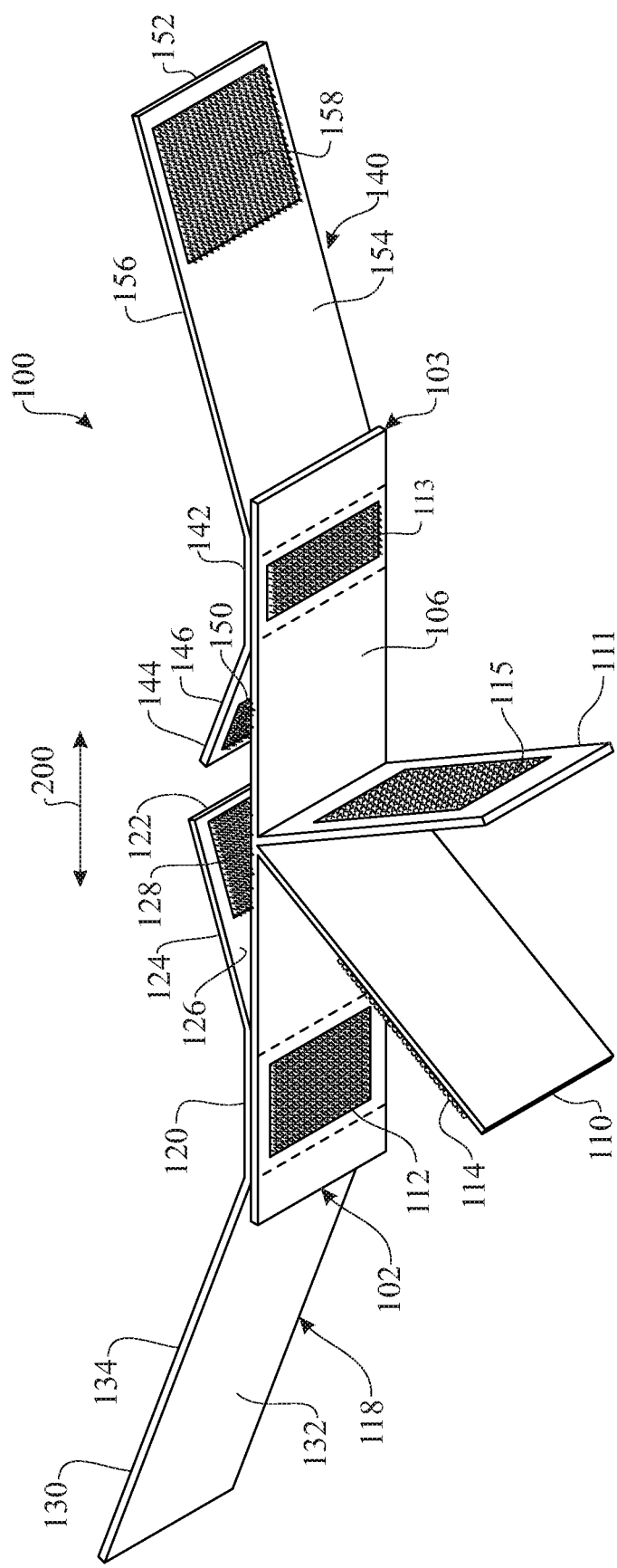
FIG. 2 presents a bottom front perspective view of the digit wrapping assembly of FIG. 1.
Figure 3:
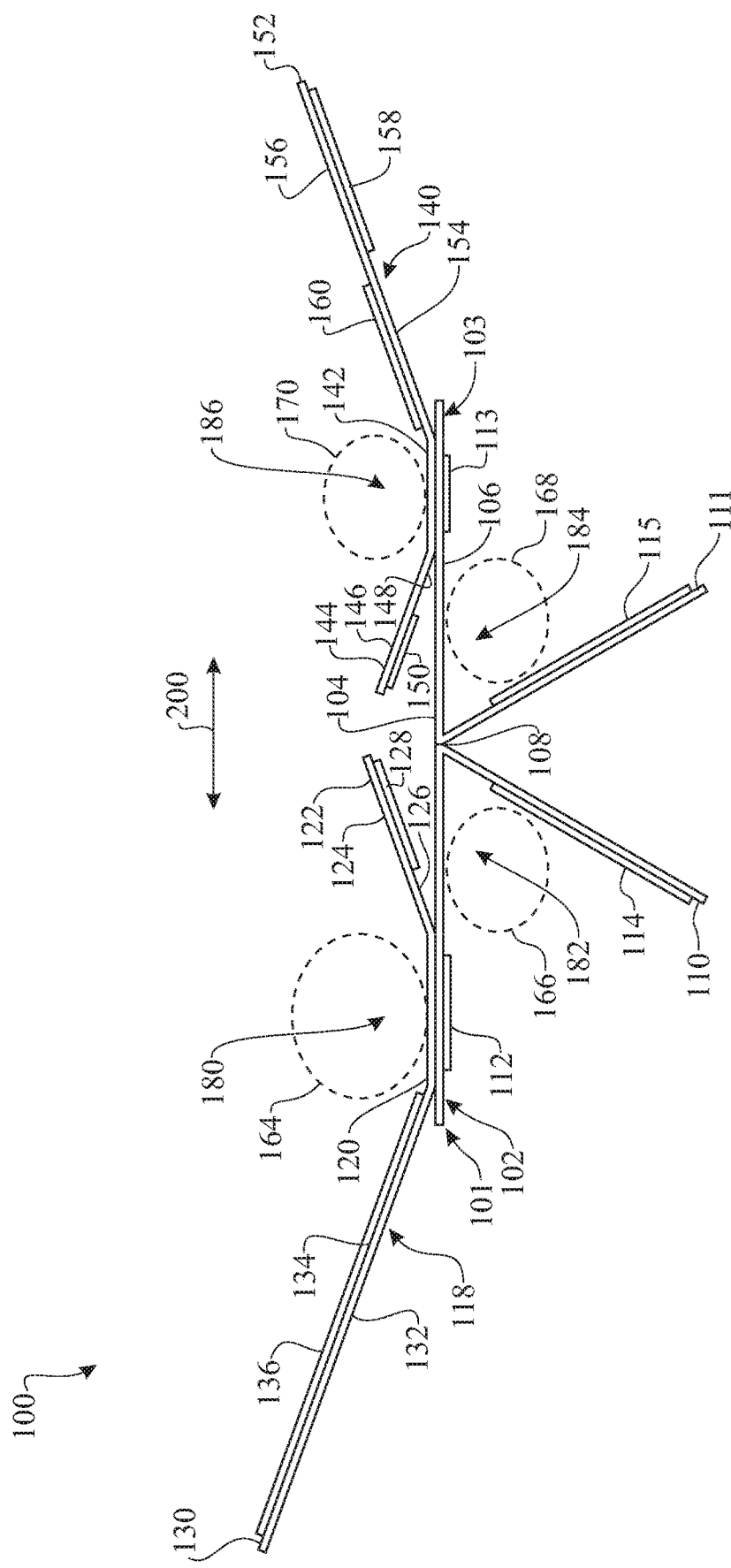
FIG. 3 presents a front elevation view of the digit wrapping assembly of FIG. further illustrating four digits in broken line format to indicate an initial placement of the four digits within the digit wrapping assembly.

Referring initially to FIGS. 1-3, a digit wrapping assembly 100 is illustrated in accordance with an exemplary embodiment of the present invention. The digit wrapping assembly 100 is generally flexible and made of flexible straps, as will be explained. As shown, the digit wrapping assembly 100 comprises a generally elongated support strap 101, formed along a longitudinal direction 200. The support strap 101 includes a first support strap portion 102 and a second support strap portion 103. In some embodiments, the support strap portions 102, 103 may be joined to each other along a strap joint 108 via stitching or other suitable attachment technique. In other embodiments, the first and second support strap portions 102 and 103 may be continuous with each other. The support strap 101 has a top surface or side 104 and a bottom surface or side 106. As will be explained in greater detail hereinafter, when applying the digit wrapping assembly 100 onto the fingers or toes of a human or animal patient, the top side 104 of the support strap 101 is to be arranged towards the fingers or toes, while the bottom side 106 of the support strap 101 is to be arranged facing away from the fingers or toes.

A first bottom fastener 112 and a second bottom fastener 113 are provided on the bottom side 106 of the support strap 101 for purposes which will be hereinafter described. The first and second bottom fasteners 112 and 113 are arranged spaced apart from one another, and preferably at or near opposite longitudinal ends of the support strap 101, In some embodiments, the first and second bottom fasteners 112, 113 may include a hook or loop element of a hook-and-loop fastener. Preferably, the first and second bottom fasteners 112, 113 consist in a hook element of a hook-and-loop fastener.

A first bottom strap portion 110 and a second bottom strap portion 111 extend from an intermediate section of the bottom side 106 of the support strap 101, the intermediate section arranged between the first and second bottom fasteners 112, 113. For instance and without limitation, as shown, the first and second bottom strap portions 110, 111 can extend from opposite sides of the strap joint 108, More specifically, in some embodiments, as shown, the first bottom strap portion 110 and the first support strap portion 102 form a single-piece strap unit which is folded in a V-shaped arrangement and stitched (substantially along the strap joint 108) to a similar V-shaped single-piece strap unit formed by the second bottom strap portion 111 and the second support strap portion 103. Alternative embodiments are contemplated, however, for constructing the first and second bottom strap portions 110, 111. For instance, the first and second bottom strap portions 110, 111 can form an integral, single-piece unit folded into a V-shape and attached to the bottom side 106 of the support strap 101. In other embodiments, the first and second bottom strap portions 110, 111 may not form a V-shape; for instance, the first and second bottom strap portions 110 and 111 may extend from the bottom side 106 of the support strap 101 in a spaced-apart relationship with one another.

The first and second bottom strap portions 110 and 111 may include a respective fastener 114 and 115. The fastener 114 of the first strap portion 110 is in facing relationship to the first bottom fastener 112 on the bottom side 106 of the support strap 101 and is complementary to said first bottom fastener 112 for engagement therewith. In turn, the fastener 115 of the second strap portion 111 is in facing relationship to the second bottom fastener 113 on the bottom side 106 of the support strap 101 and is complementary to said second bottom fastener 113 for engagement therewith. For instance, in some embodiments, the fasteners 114, 115 of the first and second bottom strap portions 110 and 111 may include a hook or loop element of a hook-and-loop fastener configured to mate with the hook or loop element of the first and second bottom strap portions 110 and 111. Preferably, the fasteners 114, 115 of the first and second bottom strap portions 110 and 111 are loop portions of a hook-and-loop fastener.

An elongated, first top strap 118 and an elongated, second top strap 140 may be attached to the top side 104 of the support strap 101, preferably at or near the opposite longitudinal ends of the support strap 101, similarly to the first and second bottom fasteners 112 and 113, respectively. The first top strap 118 may include a first strap attachment portion 120 attached to the top side 104 of the support strap 101. A first intermediate strap portion 122 may extend from the first strap attachment portion 120. A first end strap portion 130 may extend from the first strap attachment portion 120 opposite the first intermediate strap portion 122. As best shown in FIG. 2, the first intermediate strap portion 122 may have a top surface 124 and a bottom surface 126. A fastener 128 may be provided on the bottom surface 126 of the first intermediate strap portion 122. In turn, the first end strap portion 130 may have a bottom surface 132 and a top surface 134. As best shown in FIG. 1, a fastener 136 may be provided on the top surface 134. The fastener 128 on the bottom surface 126 of the first intermediate strap portion 122 and the fastener 136 on the top surface 134 of the first end strap portion 130 may be complementary to each other for engagement therebetween. In some embodiments, the fastener 128 and the fastener 136 may be complementary hook or loop elements of a hook-and-loop fastener. Preferably, the fastener 136 on the top surface 134 of the first end strap portion 130 is a loop portion of a hook-and-loop fastener, and the fastener 128 on the bottom surface 126 of the first intermediate strap portion 122 is a mating hook portion of a hook-and-loop fastener. It is to be understood that the major surfaces (e.g. planar, or curved planar) of the straps or strap portions may be invariably referred to herein as "faces". Such surfaces may be selectively and variably angled (anglable), bent, (e.g. with respect to one or more other strap portions) and wrapped around digits as disclosed herein.

With continued reference to FIGS. 1 and 2, the second top strap 140 may include a second strap attachment portion 142 attached to the top side 104 of the support strap 101. A second intermediate strap portion 144 may extend from the second strap attachment portion 142. A second end strap portion 152 may extend from the second strap attachment portion 142 opposite the second intermediate strap portion 144. The second intermediate strap portion 144 may have a top surface 146 and a bottom surface 148. A fastener 150 may be provided on the bottom surface 148 of the second intermediate strap portion 144. The second end strap portion 152 may have a bottom surface 154 and a top surface 156. A fastener 160 may be provided on the top surface 156 of the second end strap portion 152. The fastener 150 on the bottom surface 148 of the second intermediate strap portion 144 and the fastener 160 on the top surface 156 of the second end strap portion 152 are complementary to each other for engagement therebetween. In some embodiments, the fastener 150 and the fastener 160 may be complementary hook and loop elements of a hook-and-loop fastener. Preferably, the fastener 160 on the top surface 156 of the second end strap portion 152 is a loop portion of a hook-and-loop fastener, and the fastener 150 on the bottom surface 148 of the second intermediate strap portion 144 is a mating hook portion of a hook-and-loop fastener.

Furthermore, an additional fastener 158 may be provided on the bottom surface 154 of the second end strap portion 152. This fastener 158 on the bottom surface 154 of the second end strap portion 152 is arranged closer to a distal, free end of the second end strap portion 152 than the fastener 160 arranged on the opposite, top side 156 of the second end strap portion 152 for purposes that will be hereinafter described. The fastener 158 on the bottom surface 154 of the second end strap portion 152 and the fastener 136 on the top surface 134 of the first end strap portion 130 may be complementary to each other for engagement therebetween. In some embodiments, the fastener 158 and the fastener 136 may be complementary hook and loop elements of a hook-and-loop fastener. Preferably, the fastener 136 on the top surface 134 of the first end strap portion 130 is a loop portion of a hook-and-loop fastener, and the fastener 158 on the bottom surface 154 of the second end strap portion 152 is a mating, hook portion of a hook-and-loop fastener.

Various elements of the digit wrapping assembly 100 may form part of what is referred herein to as a "digit wrapping sub-assembly". For example, a digit wrapping sub-assembly for a first digit of a user may comprise the first end strap portion 130, the first strap attachment portion 120, the first intermediate strap attachment portion 122, the fastener 136 and/or the fastener 128. As another example, a digit wrapping sub-assembly for a second digit of the user may comprise the first bottom strap portion 110, the fastener 114, the first support strap portion 102, and/or the first bottom fastener 112. As yet another example, a digit wrapping sub-assembly for a third digit of the user may comprise the second bottom strap portion 111, the fastener 115, the second support strap portion 103, and/or the second bottom fastener 113. As still yet another example, a digit wrapping sub-assembly for a fourth digit of the user may comprise the second end strap portion 152, the second strap attachment portion 142, the second intermediate strap attachment portion 144, the fastener 158, and/or the fastener 150.

The support strap 101, the first and second bottom strap portions 110 and 111, and the first and second top straps 118 and 140 are preferably non-stretchable, and may be fabricated of a soft and nonwoven material.

Figure 4:
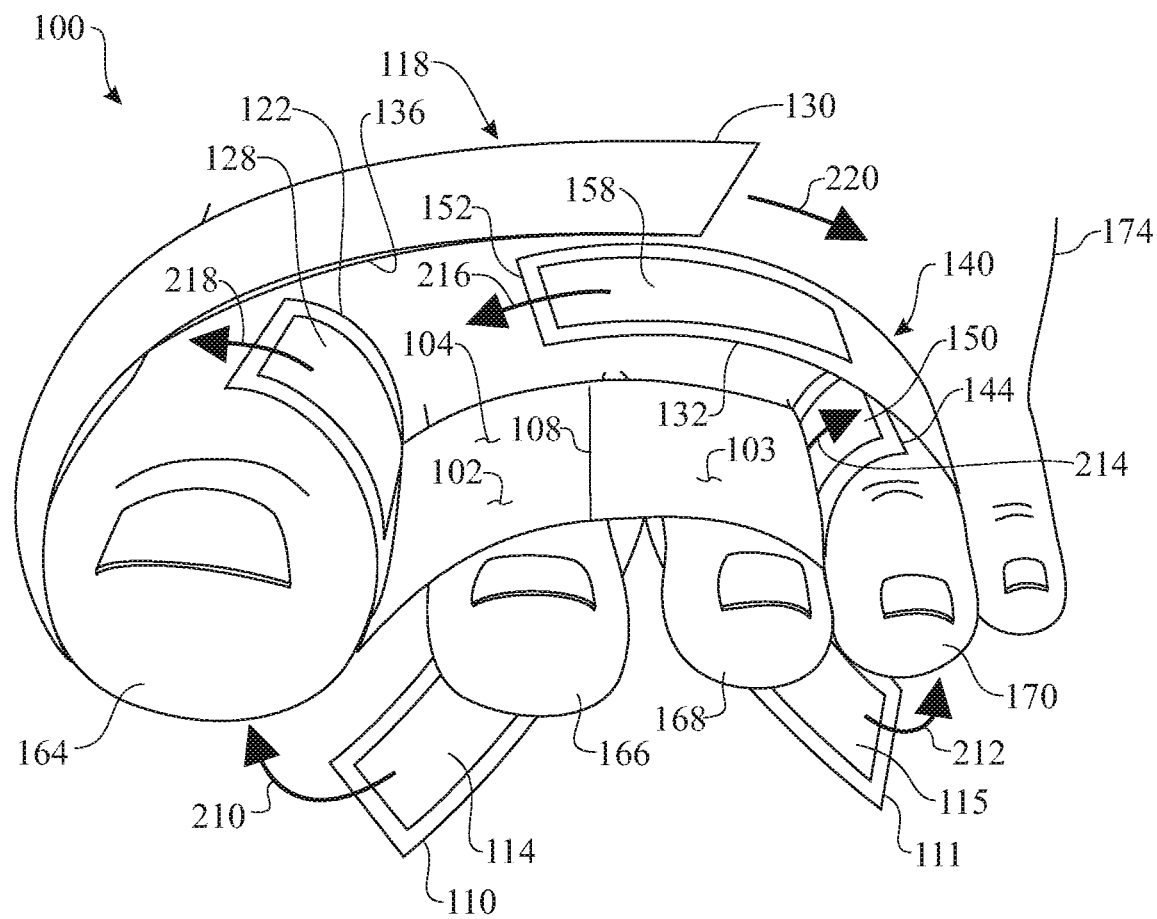
FIG. 4 presents a front perspective view of the digit wrapping assembly of the present invention being placed preparatory to wrapping of the first, second, third and fourth digits on a foot of a patient.
Figure 5:
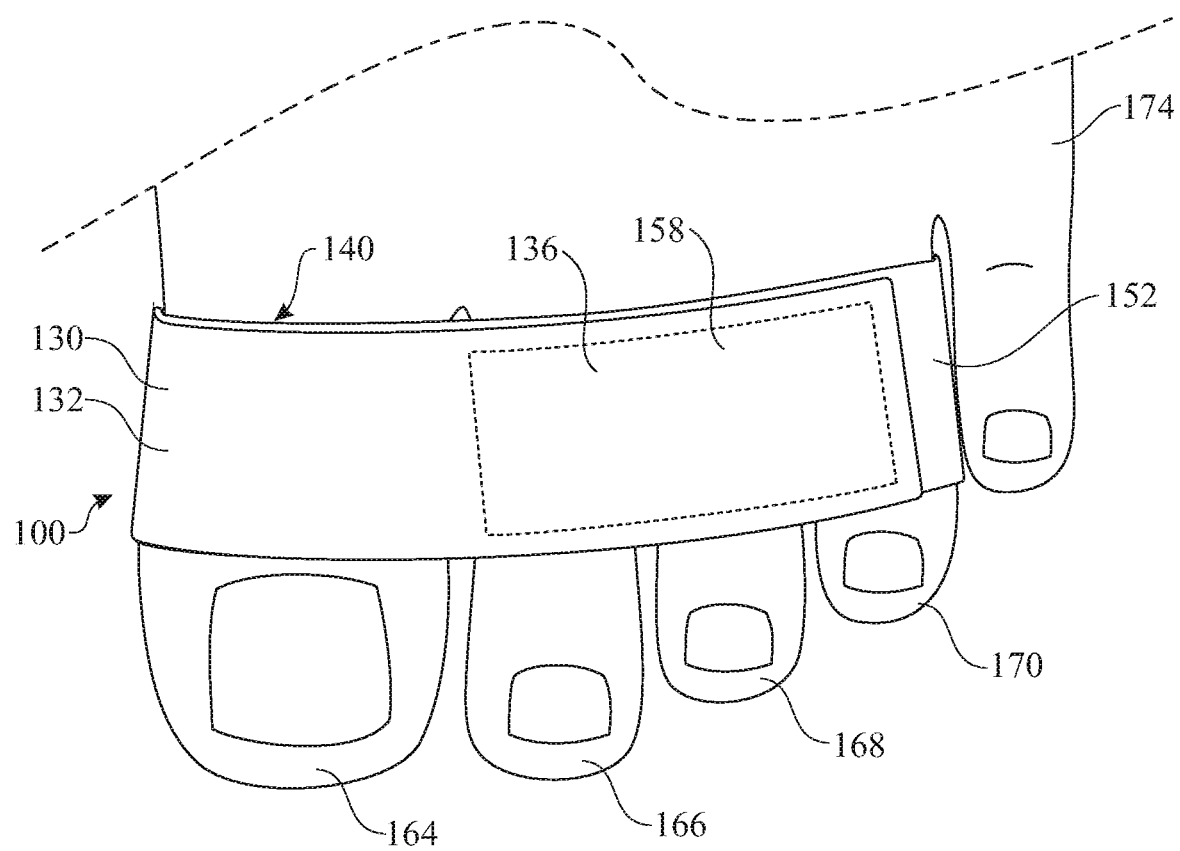
FIG. 5 presents a top plan view of the digit wrapping assembly of the present invention fastened around the digits on the foot of the patient.
Figure 6:
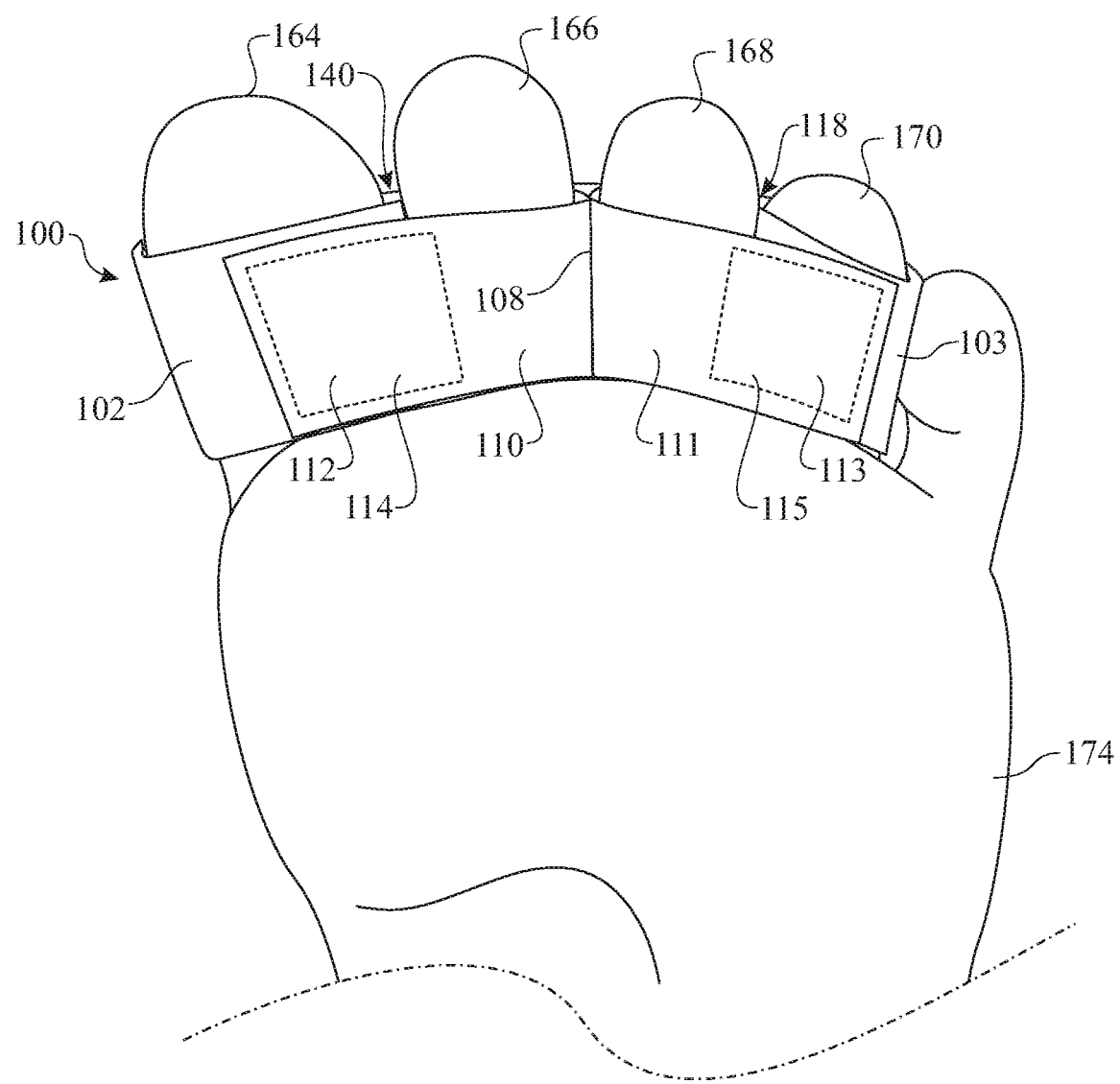
FIG. 6 is a bottom plan view of the digit wrapping assembly of the present invention fastened around the digits on the foot of the patient.

In typical application, the digit wrapping assembly 100 is used to wrap and compress digits on the hand or foot of a patient. For instance, in the non-limiting example illustrated in FIGS. 3-6, the digit wrapping assembly 100 is used to wrap and compress a first digit 164, a second digit 166, a third digit 168 and a fourth digit 170 on a foot 174 of a patient. In particular, FIG. 3 shows the digit wrapping assembly 100 in what is referred to herein as a "positioning state" in which digits 164, 166, 168, and 170 of the patient are arranged in respective positions for subsequent securing and/or compression. In the positioning state, one or more of the digit wrapping sub-assemblies described above may be unsecured and open, with their corresponding fasteners being unattached to each other. Further, as may be seen in FIG. 3, the first and fourth digits 164 and 170 may be vertically offset from the second and third digits 166 and 168 in the positioning state. Such vertical offset may be measured along a vertical direction that is substantially perpendicular to longitudinal direction 200 (FIG. 1), for example. Conversely, FIG. 4 shows the digit wrapping assembly 100 in what is referred to herein as a "securing state" in which digits 164, 166, 168, and 170 of the patient are substantially secured and compressed via disconnectable attachment of the corresponding digit wrapping sub-assemblies. As may be seen in FIG. 4, digits 164, 166, 168, and 170 may be substantially vertically aligned with one another in the securing state.

Initially, the digits 164, 166, 168 and 170 of the patient nay be positioned as illustrated in broken line format in FIG. 3. Specifically, the first digit 164 is arranged above the support strap 101, in a first space 180 delimited between the first end strap portion 130 and the first intermediate strap portion 122. The second digit 166 is arranged below the support strap 101, in a second space 182 delimited between the first support strap portion 102 of the support strap 101 and the first bottom strap portion 110. Similarly, the third digit 168 is arranged below the support strap 101, in a third space 184 delimited between the second support strap portion 103 of the support strap 101 and the second bottom strap portion 111. Placing the second and third digits 166, 168 can be achieved by inserting the first and second bottom strap portions 110, 111 between the patient's second digit 166 and the third digit 168 as better shown in FIG. 4. The fourth digit 170, in turn, is placed above the support strap 101, in a fourth space 186 delimited between the second intermediate strap portion 144 and the second end strap portion 152. The second and third spaces 182, 184 are both arranged longitudinally between the first and fourth spaces 180, 186—e.g., are both arranged inward relative to the first and fourth spaces along longitudinal direction 200.

Then, as illustrated by arrow 210 in FIG. 4, the first bottom strap portion 110 is wrapped below the second digit 166 and the fastener 114 on the first bottom strap portion 110 is attached to the companion first bottom fastener 112 on the bottom side 106 of the first support strap portion 102 of the support strap 101, thus encircling, compressing and securing the second digit 166 within the second space 182. Similarly, the second bottom strap portion 111 is wrapped below the third digit 168 as indicated by arrow 212, and the fastener 115 on the second bottom strap portion 111 is attached to the companion second bottom fastener 113 on the bottom side 106 of the second support strap portion 103 of the support strap 101, encircling, compressing and securing the third digit 168 within the third space 184.

As further illustrated in FIG. 4, the second intermediate strap portion 144 and the second end strap portion 152 may next be wrapped around the fourth digit 170 as indicated by arrows 214 and 216, respectively. The fastener 160 (FIG. 3) on the top surface 156 of the second end strap portion 152 may be attached to the companion fastener 150 on the bottom surface 148 of the second intermediate strap portion 144. Thus, the second intermediate strap portion 144 and the second end strap portion 152 of the second top strap 140 wrap and compress the fourth digit 170. As shown in FIG. 4, a leftover, distal portion of the second end strap portion 152 containing the fastener 158 remains free and unattached. Then, the first intermediate strap portion 122 and the first end strap portion 130 may be wrapped around the first digit 164 as indicated by arrows 218 and 220, respectively. The fastener 136 (FIG. 3) on the top surface 134 of the first end strap portion 130 may be attached to the companion fastener 128 on the bottom surface 126 of the first intermediate strap portion 122. Thus, the first intermediate strap portion 122 and the first end strap portion 130 of the first top strap 118 wrap and compress the first digit 164. As understood from FIG. 4, a leftover, distal portion of the first end strap portion 130 containing part of the fastener 136 remains free and unattached. Next, the first end strap portion 130 is pulled towards the fourth digit 170 as indicated by arrow 220, while the second end strap portion 152, is pulled towards the first digit 164 as indicated by arrow 216, compressing the four digits 164, 166, 168 and 170 against one another. The first end strap portion 130 is passed over the second end strap portion 152 and, when adequate digit compression is achieved, the first end strap portion 130 is pressed against the overlapped distal end of the second strap portion 152 to cause the fastener 136 (FIG. 3) on the top surface 134 of the first end strap portion 130 to fasten to the fastener 158 on the bottom surface 154 of the second end strap portion 152, reaching a final position shown in FIG. 5. Because the digit wrapping assembly 100 is generally flexible, the digit wrapping assembly 100 in the final position is deformed to allow the four spaces 180, 182, 184 and 186 (and thus four digits 164, 166, 168 and 170) to be arranged in a greater longitudinal alignment than in their initial position (FIG. 3).

The fastening sequence described heretofore can be easily and intuitively carried out by the patient. In addition, the top attachment (FIG. 5) between the first end strap portion 130 and the second end strap portion 152 and the bottom attachments (FIG. 6) between the first and second bottom strap portions 110 and 111 and the first and second support strap portions 102 and 103, respectively, are readily accessible allowing the user to easily adjust the degree of compression. For example, a large, and in some examples primary, portion of overall compression afforded by the digit wrapping assembly 100 may be adjusted by selecting the degree to which fasteners 136 and 158 overlap when attached to each other. In this example, a larger degree of attached overlap between fasteners 136 and 158 may yield a relatively greater overall level of compression, whereas a lesser degree of attached overlap between fasteners 136 and 158 may yield a relatively lesser overall level of compression. In addition, each attachment is adjustable for a customized fit and accommodates instances in which swelling may be a factor. The digit wrapping assembly 100 can be selectively removed by reversing the steps described above.

Thus, as shown, the digit wrapping assembly 100 provides a system of integrated wraps which is configured to secure and immobilize four digits of a patient, and which is further configured to secure all four digits together via a final wrap that encompasses the four digits. By incorporating these four digits, healthy adjacent digits are able to assist in the stabilization and immobilization of injured digit(s).

It will be appreciated by those skilled in the art that the digit wrapping assembly 100 is adjustable and can be used directly against the skin, or alternatively, in conjunction with wound dressings such as gauze, compression foam pads and fluid-collection pads which cover and drain surgical incisions, when necessary. In some applications, the digit wrapping assembly 100 can be used to hold or secure sterile wound dressings in place. As the needs of the patient change during the course of treatment, the digit wrapping assembly 100 can be used throughout the therapeutic, pre-surgical, post-surgical and rehabilitation stages.

The digit wrapping assembly 100 is optimal for areas that are difficult to treat, such as toes and fingers. The digit wrapping assembly 100 allows for adjustable, contoured fitting such that it fits comfortably on the hand or foot on the patient. To aid in sizing, the length of excess wrap material can be cut away, as needed. This may be particularly advantageous under circumstances in which swelling has reduced to correspondingly reduce the size of the wrapped and compressed area. To extend its usability during the course of treatment, the digit wrapping assembly 100 may be reusable and washable for prolonged use.

The digit wrapping assembly 100 has shown favorable results which have not been achieved using conventional methods and procedures. The digit wrapping assembly 100 provides an innovative device that is useful for patients having a wide range of medical issues related to the toes and/or fingers, Although conventional wrapping and compressing devices attempt to wrap and/or immobilize, the mechanical structure of the digit wrapping assembly 100 provides exceptional stabilization qualities along with overall comfort that conventional methods and procedures cannot provide.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A digit wrapping assembly, comprising:
   a support strap comprising a first support strap portion and a second support strap portion;
   a digit wrapping sub-assembly adapted for a first digit to be disposed on a top surface of the support strap, the digit wrapping sub-assembly for the first digit comprises a first end strap portion having a distal, free end opposing a first intermediate strap attachment portion also having a distal, free end, the first end strap portion and the first intermediate strap attachment portion separated from each other by a first strap attachment portion affixed to a top surface of the first support strap portion proximate a first end of the support strap, wherein the first end strap portion is longer in length than the length of the first intermediate strap attachment portion, and the digit wrapping sub-assembly for the first digit comprising selectively and variably anglable opposing faces;
   a digit wrapping sub-assembly adapted for a second digit comprising a selectively and variably anglable face having a distal, free end that extends from a bottom surface of the first support strap portion; and
   a digit wrapping sub-assembly adapted for a third digit comprising a selectively and variably anglable face having a distal, free end that extends from a bottom surface of the second support strap portion, wherein the distal, free end of the digit wrapping sub-assembly of the second digit is movable in an opposable direction from the distal, free end of the digit wrapping sub-assembly of the third digit, and vice-a-versa,
   each of the selectively and variably anglable faces comprises a fastener configured for disconnectable attachment with a corresponding fastener,
   in a positioning state of the digit wrapping assembly wherein one or more of the digit wrapping sub-assemblies are unsecured and open, with their corresponding fasteners unattached to each other, the digit wrapping assembly is configured to receive the first digit at a vertical offset from the second and third digits, wherein positioning of the first digit comprises positioning the first digit above the support strap, and positioning the second and third digits comprises positioning the second and third digits below the support strap, and
   in a securing state of the digit wrapping assembly, the digit wrapping assembly is configured to place the first, second, and third digits substantially horizontally aligned with one another, wherein the first digit is separated from the second and third digit by at least the support strap, and the second digit and the third digit are separated from one another by at least one digit wrapping sub-assembly.

2. The digit wrapping assembly of claim 1, wherein the first end strap portion and the first intermediate strap attachment portion comprises respective opposing fasteners configured for disconnectable attachment with each other.

3. The digit wrapping assembly of claim 1, further comprising a digit wrapping sub-assembly for a fourth digit disposed on the top surface of the support strap, the digit wrapping sub-assembly for the fourth digit comprising selectively and variably anglable opposing faces configured for disconnectable attachment with one another, and wherein positioning of the fourth digit comprises positioning the fourth digit above the support strap.

4. The digit wrapping assembly of claim 3, wherein one of the selectively and variably anglable opposing faces of the digit wrapping sub-assembly for the fourth digit is configured for disconnectable attachment with one of the selectively and variably anglable opposing faces of the digit wrapping sub-assembly for the first digit, and wherein the positioning of the first digit is within a first space delimited between the first end strap portion and the first intermediate strap portion and of the digit wrapping assembly, the positioning of the second digit is within a second space delimited between the first support strap portion and a first bottom strap portion of the digit wrapping assembly, the positioning of the third digit is within a third space delimited between the second support strap portion and a second bottom strap portion of the digit wrapping assembly, the positioning of the fourth digit is within a fourth space delimited between a second end strap portion and a second intermediate strap portion and of the digit wrapping assembly, and at least partially enclosing one or more of the first, second, third, and fourth spaces to thereby secure and compress one or more of the first, second, third, and fourth digits therein, respectively.

5. The digit wrapping assembly of claim 3, wherein the digit wrapping sub-assembly for the fourth digit comprises a second end strap portion opposing a second intermediate strap attachment portion, the second end strap portion and the second intermediate strap attachment portion being separated from each other by a second strap attachment portion.

6. The digit wrapping assembly of claim 5, wherein the second strap attachment portion is disposed on a top surface of the second support strap portion toward a second end of the support strap.

7. The digit wrapping assembly of claim 1, wherein the fastener of the selectively and variably anglable face of the digit wrapping sub-assembly for the second digit is configured for disconnectable attachment with a fastener disposed on the bottom surface of the first support strap portion, and wherein the fastener of the selectively and variably anglable face of the digit wrapping sub-assembly for the third digit is configured for disconnectable attachment with a fastener disposed on the bottom surface of the second support strap portion.

8. A digit wrapping assembly contoured to fit fingers or toes of a user, comprising:
- a flexible support;
- a flexible, first end strap portion extending from the support at or near a first longitudinal end thereof, and a flexible, second end strap portion extending from the support at or near an opposite, second longitudinal end thereof, wherein the first end strap portion and the second end strap portion each have a distal, free end;
- a flexible, first intermediate strap portion and a flexible, second intermediate strap portion extending from an intermediate region of a top side of the support, the first intermediate strap portion being of a smaller strap length than the first end strap portion, and the second intermediate strap portion being of a smaller strap length than the second end strap portion; and
- a flexible, first bottom strap portion and a flexible, second bottom strap portion extending from a bottom side of the support; wherein
- the first intermediate strap portion and the first end strap portion face one another, the first intermediate strap portion disconnectably attachable to a lower portion of the first end strap portion that is a distance from an end edge of the distal, free end of the first end strap portion to encircle a first space,
- the first bottom strap portion and the support face one another and are disconnectably attachable to one another to encircle a second space,
- the second bottom strap portion and the support face one another and are disconnectably attachable to one another to encircle a third space,
- the second intermediate strap portion and the second end strap portion face one another and are disconnectably attachable to one another to encircle a fourth space, and
- the first end strap portion is extendable over and attachable to the second end strap portion, and
- wherein in a positioning state of the digit wrapping assembly wherein one or more of the flexible, first end strap portion, the flexible, second end strap portion, the flexible, first intermediate strap portion, and the flexible, second intermediate strap portion, are unsecured and open, and the digit wrapping assembly is configured to receive a first digit and a fourth digit at a vertical offset from a second and a third digit, and positioning of the first and fourth digits comprises positioning the first and fourth digits above the flexible support within the first and fourth spaces, respectively, and positioning the second and third digits comprises positioning the second and third digits below the flexible support within the second and third spaces, respectively, such that in the positioning state of the digit wrapping assembly the first and fourth spaces are vertically offset, about the flexible support, from the second and third spaces.

9. The digit wrapping assembly of claim 8, wherein
in a securing state of the digit wrapping assembly, the first, second, third, and fourth spaces are substantially horizontally aligned with one another, and
a degree of overlap between the first end strap portion and the second end strap portion is adjustable to adjust a degree of compression applied to one or more digits respectively positioned in the first, second, third, and fourth spaces.

* * * * *